United States Patent [19]

Clemens et al.

[11] Patent Number: 5,106,836
[45] Date of Patent: Apr. 21, 1992

[54] ENTERAL DIET

[75] Inventors: Roger D. Clemens, Reseda, Calif.; James Martucci, Libertyville, Ill.; W. Bruce Rowe, Evanston, Ill.; Irene Wei, Westmont, Ill.

[73] Assignee: Clintec Nutrition Co., Deerfield, Ill.

[21] Appl. No.: 658,802

[22] Filed: Feb. 22, 1991

[51] Int. Cl.$^5$ .................. A61K 37/18; A61K 37/02; A61K 31/195
[52] U.S. Cl. ...................... 514/21; 514/824; 530/833; 426/656
[58] Field of Search ............ 514/21, 824; 530/833; 426/656

[56] References Cited

U.S. PATENT DOCUMENTS 5,032,608  7/1991  Dudrick .............................. 514/396

OTHER PUBLICATIONS

Ornish, Dean, et al., (1990): Can Lifestyle Changes Reverse Coronary Heart Disease? *The Lancet*, vol. 336, pp. 129-133.

*Animal and Vegetable Proteins in Lipid Metabolism Find Atherosclerosis*, pp. 1-7, 9-17, and 85-100, (1983), Alan R. Liss, New York, N.Y.

Dudrick, Stanley J., (1987); Regression of Artherosclerosis by the Intravenous Infusion of Specific Biochemical Nutrient Substrates in Animals and Humans, *Annals of Surgery*, vol. 206, No. 3, pp. 296-315.

*Primary Examiner*—Howard E. Schain
*Assistant Examiner*—Choon Koh

[57] ABSTRACT

A composition comprising arginine enriched whey protein can be used in the formulation of a variety of simulated food products to provide a substantially fat free, calorie controlled diet which delivers high levels of protein having a hypocholesterolemic amino acid profile.

9 Claims, No Drawings

ENTERAL DIET

This invention relates to the development of substantially fat free, controlled calorie enteral diet which delivers protein having a hypocholesterolemic amino acid profile when digested and absorbed.

BACKGROUND OF THE INVENTION

It has been reported in the literature that the reduction of elevated plasma cholesterol will decrease the risk of myocardial infarction secondary to atherosclerotic coronary heart disease in humans. It has been documented that plasma cholesterol levels decline to low levels in patients who are maintained on a total parenteral nutrition (TPN) program for extended periods of time. In such a program, all of the nutritional requirements are provided by the intravenous infusion of a solution containing a desired combination of amino acids, essential vitamins, minerals and trace elements, as well as dextrose for non protein caloric requirements.

Infusion of a modified fat free TPN amino acid formulation, Atheromine ™, has been reported to induce a significant reduction in plasma cholesterol levels accompanied by regression of atherosclerosis in both animals and humans. "Regression of Atherosclerosis by the Intravenous Infusion of Specific Biochemical Nutrient Substrates in Animals and Humans", Dudrick, S. J., *Annals of Surgery*, Vol. 206, No. 3, pages 296-315 (1987), the disclosure of which is incorporated herein by reference. Atheromine ™ amino acid formulation is disclosed in U.S. patent application Ser. No. 287,620, filed Dec. 16, 1988 for Method and Substrate Composition for Treating Atherosclerosis, the disclosure of which is herein incorporated by reference. In that study correlations between plasma amino acids and plasma cholesterol levels were demonstrated using a totally intravenous fat free diet containing 18 L-amino acids formulated in quantities and ratios deemed optimal for reducing plasma cholesterol levels in each patient. A number of amino acids, namely arginine, phenylalanine, isoleucine, valine, serine, aspartic acid and leucine were found to have a very strong inverse correlation between plasma amino acids and plasma cholesterol levels. However, in that study the reduction in plasma cholesterol levels and regression of atherosclerosis were limited to the direct intravenous infusion of the Atheromine ™ amino acid solution. Oral administration of the amino acid composition was found to be ineffective in animals and humans in reducing plasma cholesterol or inducing regression of atherosclerosis.

SUMMARY OF THE INVENTION

The present invention is directed to oral and enteral dietary formulations which are substantially fat free and which deliver protein having a hypocholesterolemic amino acid profile when digested and absorbed, and to a composition for use in preparing such dietary formulations. As used herein, the term "substantially fat free" means a diet which provides less than 2 grams fat per day, with less than 1% of total calories as fat. The dietary formulations of the invention are based on the combination of L-arginine and whey protein, such as whey protein isolate having a protein content of at least 95% (N×6.38) (dry basis), to provide a composition useful in preparing a number of enteral food products which have an amino acid profile comparable to Atheromine ™.

In addition to whey protein isolate and L-arginine, the composition may contain ingredients such as maltodextrin and starch, as well as one or more gums, thickening agents, flavors, and the like to provide desired caloric, nutritional and/or functional requirements. The whey protein in the composition preferably is produced by ion exchange from an aqueous whey source to provide whey protein isolate having a protein content of more than 95% and containing less than 1% of fat and lactose. The use of this high purity whey protein isolate not only provides superior nutritional values, but a variety of functional properties as well, such as foaming, gelling, water binding, fat binding and emulsifying, making the isolate a highly versatile ingredient. The arginine enriched whey protein composition can be used in preparing a wide variety of substantially fat free, controlled calorie food products having the desired amino acid profile, with the food products thus prepared being used in an extended enteral diet which delivers protein having a hypocholesterolemic amino acid profile when digested and absorbed. For example, the arginine enhanced whey protein isolate may be used to prepare both solid and liquid foods such as crepes, pasta, pasta sauce, pancakes, soups, french toast, banana loaf, mushroom omelet, and the like which are substantially fat free and have a controlled calorie level.

During digestion, proteins are hydrolysed to their constituent amino acids which are absorbed in the blood stream. Since the arginine enhanced whey protein composition and the enteral foods prepared with the composition have an amino acid profile comparable to the Atheromine ™ TPN solution used in the Dudrick study discussed above, it appears that the enteral foods will, when digested and absorbed, deliver into the blood stream an amino acid profile having hypocholesterolemic properties. Accordingly, it is believed that humans having an elevated total plasma cholesterol will exhibit a significant reduction in total plasma cholesterol and regression of atherosclerosis when maintained on the enteral diet of the present invention.

DETAILED DESCRIPTION

In accordance with the present invention, enteral foods having a desired amino acid profile and nutritional requirements and which are suitable for use in preparing a substantially fat free enteral diet having a hypocholesterolemic amino acid profile are provided through the use of a composition of containing L-arginine and whey protein such as whey protein isolate which contains on a dry basis at least 95% protein (N×6.38) and less than 1% fat and lactose. The low levels of fat and lactose provide the whey protein with superior functionality and nutrition, enabling it to be used in a variety of enteral nutritional compositions. A preferred source of high purity whey protein is BiPRO ®, available from Le Sueur Isolates, Le Sueur, Minn. BiPRO ®, which is produced by the hydrophilic ion exchange treatment of whey, contains over 95% protein (dry basis), less than 3% mineral salts, and less than 1% fat and lactose, with the protein being undenatured and therefore fully soluble. The use of BiPRO ® is advantageous in the present invention for it not only provides superior nutritional values, but its functional properties such as foaming, gelling, and emulsifying make it highly versatile. For example BiPRO ® forms a tough but elastic gel upon heating, enabling a variety of products to be formulated from the arginine enriched BiPRO ® composition.

Whey protein isolate is enriched with sufficient L-arginine to provide a composition having excellent nutritional values and an amino acid profile comparable to the Atheromino ™ parenteral solution disclosed in U.S. patent application Ser. No. 287,620 entitled: "METHOD AND SUBSTRATE COMPOSITION FOR TREATING ATHEROSCLEROSIS," filed on Dec. 16, 1988 referred to hereinabove which was successfully used in the Dudrick study to reduce plasma cholesterol levels. Table 1 below sets out an amino acid profile comparison of the protein content of the Atheromine ™ parenteral solutions tested, BiPRO ® whey protein isolate, and an arginine enriched whey protein composition of this invention obtained by adding 0.16 parts by weight of L-arginine per part by weight of BiPRO ® whey protein isolate.

TABLE 1

AMINO ACID PROFILE COMPARISON
(Percent by Weight)

| Amino Acid | Atheromine ™ | BiPRO ® | ARG-enriched BiPRO ® |
|---|---|---|---|
| Isoleucine | 4.0–10.0 | 4.77 | 4.09 |
| Leucine | 5.0–10.0 | 12.44 | 10.67 |
| Lysine | 4.5–6.5 | 9.35 | 8.02 |
| Methionine & Cysteine | 3.5–6.5 | 4.21 | 3.61 |
| Phenylalanine & Tyrosine | 4.5–8.5 | 6.64 | 5.70 |
| Threonine | 2.0–3.5 | 4.40 | 3.71 |
| Tryptophane | 1.0–2.5 | 1.78 | 1.52 |
| Valine | 4.0–9.0 | 4.49 | 3.85 |
| Alanine | 7.0–16.0 | 4.49 | 3.85 |
| Arginine | 9.0–18.0 | 2.62 | 16.49 |
| Histidine | 1.5–3.5 | 9.35 | 8.02 |
| Proline | 4.5–8.5 | 4.30 | 3.69 |
| Serine | 2.5–6.5 | 4.49 | 3.85 |
| Glycine | 3.0–8.0 | 1.50 | 1.28 |
| Glutamic Acid | 3.5–5.5 | 14.97 | 12.83 |
| Aspartic Acid | 2.0–4.0 | 10.20 | 8.74 |
| | | 100.00 | 100.00 |

The arginine enriched whey protein composition is substantially fat free and, due to the superior functionality of the high purity, whey protein, may be formulated into a wide variety of enteral foods to provide a substantially fat free, controlled calorie diet delivering high levels of protein with a hypocholesterolemic amino acid profile.

Preferably the whey protein isolate and arginine are combined with one or more additional ingredients which provide the composition with a desired level of nutrition or with certain functional characteristics. For example, maltodextrin and/or starch may be included for non-protein caloric requirements. One or more non-nutritive materials may also be included for controlling the texture of foods formulated from the composition, such as hydrocolloids, polysaccharides, and the like to function as a thickener, gelling agent, etc. in the composition.

A suitable formulation for preparing foods used in a substantially fat free, controlled calorie diet which delivers a high level of protein having a hypocholesterolemic amino acid profile is set out in Table 2. the formulation is prepared by mixing the ingredients, in the amounts indicated, in 100 ml water.

TABLE 2

| Ingredient | Amount (gm) | Protein (gm) | CHO (gm) | Fat (gm) | Kcal |
|---|---|---|---|---|---|
| BiPRO ® whey protein isolate | 13.77 | 13.00 | 0.01 | 0.00 | 52.08 |

TABLE 2-continued

| Ingredient | Amount (gm) | Protein (gm) | CHO (gm) | Fat (gm) | Kcal |
|---|---|---|---|---|---|
| Starch | 10.00 | | 9.50 | | 38.00 |
| Maltodextrin, DE4 | 6.50 | | 6.18 | | 24.70 |
| L-Arginine | 2.16 | 2.12 | | | 8.47 |
| Flavor | 0.20 | | | | 0.00 |
| Xanthan gum | 0.10 | | | | 0.00 |
| Carrageenan | 0.10 | | | | 0.00 |
| TOTAL | 32.83 | 15.12 | 15.69 | 0.00 | 123.24 |

The arginine enriched whey protein composition, either in the form of a dry mix or as an aqueous composition may be used to prepare a wide variety of simulated food products for use in a calorie controlled, substantially fat free enteral diet. Set out in Table 3 below is a representative seven day rotational diet based on the arginine enriched whey protein isolate composition, which is formulated to provide a 70 kg person approximately 1800 Kilocalories and no more than 2 gms of fat per day while delivering a high level of protein having a hypocholesterolemic amino acid profile.

TABLE 3

Menu #1 - 1800 Calories

| MEAL | AMOUNT | EXCHANGE | FAT GRAMS |
|---|---|---|---|
| BREAKFAST | | | |
| Banana Pancakes | 100 g | 2 Protein Powder | 0.1 |
| Unsweetened Orange Juice | 8 oz | 2 Fruit | 0.2 |
| Canned Pear Halves - Juice Pack (no sugar added) | 2 halves | 1 Fruit | 0.1 |
| Syrup | 1 Tbsp | Free | 0.0 |
| Sugar-Free Syrup | 1 Tbsp | Free | 0.0 |
| SNACK | | | |
| Breadsticks | 150 g | 3 Protein Powder | 0.15 |
| Canned Fruit Cocktail | 1 cup | 2 Fruit | 0.0 |
| LUNCH | | | |
| Beef Stir-Fry | 100 g | 2 Protein Powder | 0.1 |
| Onion, Frozen Veggies | | 2 Vegetable | 0.375 |
| Canned Peaches - Juice Pack (no sugar added) | 4 halves | 2 Fruit | 0.0 |
| Rice Cakes | 2 cakes | 1 Grain | 0.0 |
| Diet Beverage | 8 oz | | 0.0 |
| with Starch Powder | 10 g | 1 Starch Powder | 0.0 |
| SNACK | | | |
| "French Fries" | 150 g | 3 Protein Powder | 0.15 |
| Canned Cherries (no sugar added) | ¼ c | 1 Fruit | 0.0 |
| DINNER | | | |
| Vegetarian Pizza | 100 g | 2 Protein Powder | 0.1 |
| Fresh Green Pepper, Mushrooms, Onion | | 1 Vegetable | 0.3 |
| Frozen Broccoli, steamed | ¼ cup | ¼ Vegetable | 0.1 |
| Unsweetened Pineapple | 1 cup | 2 Fruit | 0.0 |
| SNACK | | | |
| Corn Bread | 150 g | 3 Protein Powder | 0.15 |
| Unsweetened Grape Juice | ¼ cup | 1 Fruit | 0.1 |
| with Starch Powder | 10 g | 1 Starch Powder | 0.0 |
| | TOTAL GRAMS OF FAT: | | 1.925 |
| | TOTAL FAT EXCHANGES: | | 19¼ |
| | TOTAL KILOCALORIES: | | 1806 |
| | TOTAL GRAMS OF PROTEIN: | | 120.3 |

Reference to Protein Powder is to the use of the arginine enriched whey protein of the present invention which is

TABLE 3-continued used to create the entree that includes protein. Pursuant to the present invention, this provides the substantially fat free Enteral Diet. Examples of recipes for creating the entree using the protein powder are set forth after the seven day diet.

Menu #2 - 1800 Calories

| MEAL | AMOUNT | EXCHANGE | FAT GRAMS |
|---|---|---|---|
| BREAKFAST | | | |
| Cinnamon Applesauce Cake | 150 g | 3 Protein Powder | 0.15 |
| Unsweetened Applesauce | ¼ cup | ½ Fruit | 0.05 |
| Unsweetened Pineapple Juice with Starch Powder | ½ cup | 1 Fruit | 0.0 |
| | 10 g | 1 Starch Powder | 0.0 |
| LUNCH | | | |
| Potato Asparagus Soup | 100 g | 2 Protein Powder | 0.1 |
| Canned Asparagus, Onion | | 1½ Vegetable | 0.4 |
| Wheat Cakes | 4 cakes | 2 Grain | 0.0 |
| Peach Nectar | ⅔ cup | 2 Fruit | 0.0 |
| with Starch Powder | 10 g | 1 Starch Powder | 0.0 |
| SNACK | | | |
| Popsnacks | 200 g | 4 Protein Powder | 0.2 |
| Cranberry Juice | ½ c | 1 Fruit | 0.1 |
| DINNER | | | |
| Pasta | 150 g | 3 Protein Powder | 0.15 |
| Tomato Sauce (NO OIL) | ¼ cup | 1 Vegetable | 0.15 |
| Fresh Zucchini, cooked | 1 cup | 1 Vegetable | 0.1 |
| Wasa Crisp Bread (Hearty Rye) | 1½ slices | 1 Grain | 0.0 |
| Unsweetened Orange Juice | 1 cup | 2 Fruit | 0.2 |
| with Starch Powder | 10 g | 1 Starch Powder | 0.0 |
| SNACK | | | |
| Crepes | 150 g | 3 Protein Powder | 0.15 |
| Boysenberry Sauce | ½ cup | 1 Fruit | 0.15 |
| with Starch Powder | 10 g | 1 Starch Powder | 0.0 |
| | TOTAL GRAMS OF FAT: | | 1.90 |
| | TOTAL FAT EXCHANGES: | | 19 |
| | TOTAL KILOCALORIES: | | 1804 |
| | TOTAL GRAMS OF PROTEIN: | | 129.2 |

Menu #3 - 1800 Calories

| MEAL | AMOUNT | EXCHANGE | FAT GRAMS |
|---|---|---|---|
| BREAKFAST | | | |
| Scrambled Eggs with Vegetables Fresh Onion, Green Pepper | 100 g | 2 Protein Powder | 0.1 |
| | | 1 Vegetable | 0.14 |
| Unsweetened Grapefruit Juice with Starch Powder | ½ cup | 1 Fruit | 0.1 |
| | 10 g | 1 Starch Powder | 0.0 |
| SNACK | | | |
| Carrot Sponge Cake | 100 g | 2 Protein Powder | 0.1 |
| Shredded Carrots, raw | ½ cup | 1 Vegetable | 0.1 |
| Lemonade, frozen concentrate with Starch Powder | 1½ cup | 2½ Fruit | 0.0 |
| | 10 g | 1 Starch Powder | 0.0 |
| LUNCH | | | |
| Croutons | 100 g | 2 Protein Powder | 0.1 |
| Iceberg Lettuce | 2½ leaves | ½ Vegetable | 0.1 |
| Boiled Red Beets | 1 cup | 2 Vegetable | 0.0 |
| Tasti-Diet Dressing (oil and sugar-free) | 1 Tbsp | Free | 0.0 |
| Canned Mandarin Orange | ½ cup | ½ Fruit | 0.05 |
| SNACK | | | |
| Crunchy Carrots (raw) | 1½ cup | 3 Vegetable | 0.3 |
| with Bacon | 150 g | 3 Protein Powder | 0.15 |
| Unsweetened Apple Juice | ½ cup | 1 Fruit | 0.1 |
| with Starch Powder | 10 g | 1 Starch Powder | 0.0 |
| DINNER | | | |
| Spoon Burger | 100 g | 2 Protein Powder | 0.1 |
| Veggies in Recipe | | 1 Vegetable | 0.169 |
| San Rice Cakes | 4 cakes | 2 Grain | 0.0 |
| Apricot Nectar | ½ cups | 1 Fruit | 0.1 |
| with Starch Powder | 10 g | 1 Starch Powder | 0.0 |
| SNACK | | | |
| Pumpkin Pie Squares | 100 g | 2 Protein Powder | 0.1 |
| Canned Pumpkin | ½ cup | 1 Vegetable | 0.17 |
| Unsweetened Pineapple Juice | 1 cup | 2 Fruit | 0.0 |
| with Starch Powder | 10 g | 1 Starch Powder | 0.0 |
| | TOTAL GRAMS OF FAT: | | 1.98 |
| | TOTAL FAT EXCHANGES: | | 19¼ |
| | TOTAL KILOCALORIES: | | 1797 |
| | TOTAL GRAMS OF PROTEIN: | | 122.7 |

Menu #4 - 1800 Calories

| MEAL | AMOUNT | EXCHANGE | FAT GRAMS |
|---|---|---|---|
| BREAKFAST | | | |
| French Toast | 150 g | 3 Protein Powder | 0.15 |
| *Syrup | 2 Tbsp | Free | 0.0 |
| **Sugar-Free Syrup | 3 Tbsp | Free | 0.0 |
| Figs | 2 Figs | ½ Fruit | 0.1 |
| Diet Beverage | 1 cup | Free | 0.0 |
| with Starch Powder | 10 g | 1 Starch Powder | 0.0 |
| SNACK | | | |
| Kellogg's Product 19 | 1 cup | 1¼ Grain | 0.0 |
| Peach Nectar | 1 cup | 3 Fruit | 0.0 |
| with Starch Powder | 10 g | 1 Starch Powder | 0.0 |
| LUNCH | | | |
| Polynesian Chicken | 200 g | 4 Protein Powder | 0.2 |
| Snap Green Beans, canned | 1 cup | 1 Vegetable | 0.1 |
| Grapefruit, raw | 1 half | ½ Fruit | 0.1 |
| Diet Beverage | 1 cup | Free | 0.0 |
| with Starch Powder | 10 g | 1 Starch Powder | 0.0 |
| SNACK | | | |
| Onion Squares | 100 g | 2 Protein Powder | 0.1 |
| Fresh Onions | ½ cup | ½ Vegetable | 0.1 |
| Fresh Cucumbers | 2 cups | 1 Vegetable | 0.2 |
| Tasti-Diet Dressing (oil and sugar-free) | 1 Tbsp | Free | 0.0 |
| Unsweetened Apple Juice | ½ cup | 1 Fruit | 0.1 |
| with Starch Powder | 10 g | 1 Starch Powder | 0.0 |
| DINNER | | | |
| Broccoli Tomato Quiche | 100 g | 2 Protein Powder | 0.1 |
| Fresh Onion, Tomato, Broccoli | | 1¾ Vegetable | 0.35 |
| Boiled Zucchini Squash | 1 cup | 1 Vegetable | 0.1 |
| Canned Peach Halves Juice Pack (no sugar added) | 4 halves | 2 Fruit | 0.0 |
| Diet Beverage | 1 cup | Free | 0.0 |
| with Starch Powder | 10 g | 1 Starch Powder | 0.0 |
| SNACK | | | |
| Tangy Orange Bars | 200 g | 4 Protein Powder | 0.2 |
| Unsweetened Orange Juice | ½ cup | 1 Fruit | 0.1 |
| with Starch Powder | 10 g | 1 Starch Powder | 0.0 |
| | TOTAL GRAMS OF FAT: | | 2.0 |
| | TOTAL FAT EXCHANGES: | | 20 |
| | TOTAL KILOCALORIES: | | 1805 |
| | TOTAL GRAMS OF PROTEIN: | | 128.3 |

Menu #5 - 1800 Calories

FAT

TABLE 3-continued

| MEAL | AMOUNT | EXCHANGE | GRAMS |
|---|---|---|---|
| BREAKFAST | | | |
| Cinnamon Applesauce Cake | 150 g | 3 Protein Powder | 0.15 |
| Unsweetened Applesauce | ¼ cup | ½ Fruit | 0.0 |
| Canned Fruit Cocktail Juice Pack (no sugar added) with Starch Powder | ¼ cup | 1 Fruit | 0.0 |
| | 10 g | 1 Starch Powder | 0.0 |
| LUNCH | | | |
| Shrimp Stuffed Tomato | 50 g | 1 Protein Powder | 0.05 |
| Fresh Tomato | 1 large | 1 Vegetable | 0.3 |
| Fresh Onion, Green Pepper | ¼ cup | ½ Vegetable | 0.1 |
| "Mashed Potatoes" | 100 g | 2 Protein Powder | 0.1 |
| Unsweetened Apple Juice | 1 cup | 2 Fruit | 0.2 |
| SNACK | | | |
| Green Beans With Ham | 100 g | 2 Protein Powder | 0.1 |
| Canned Green Beans, Water Chestnuts, & Raw Celery | | 1½ Vegetable | 0.07 |
| Sesame Cakes | 2 cakes | 1 Grain | 0.0 |
| DINNER | | | |
| Chicken Loaf | 200 g | 4 Protein Powder | 0.2 |
| Long Grain White Rice, cooked | ¼ cup | 1 Grain | 0.0 |
| Unsweetened Applesauce | ¼ cup | 1 Fruit | 0.1 |
| Unsweetened Grape Juice with Starch Powder | 1 cup | 3 Fruit | 0.3 |
| | 10 g | 1 Starch Powder | 0.0 |
| SNACK | | | |
| Canned Peaches - Juice Pack (no sugar added) | 4 halves | 2 Fruit | 0.0 |
| Breadsticks | 150 g | 3 Protein Powder | 0.15 |
| TOTAL GRAMS OF FAT: | | | 1.87 |
| TOTAL FAT EXCHANGES: | | | 18¾ |
| TOTAL KILOCALORIES: | | | 1801 |
| TOTAL GRAMS OF PROTEIN: | | | 124.7 |

Menu #6 - 1800 Calories

| MEAL | AMOUNT | EXCHANGE | FAT GRAMS |
|---|---|---|---|
| BREAKFAST | | | |
| Cinnamon Raisin Bread | 100 g | 2 Protein Powder | 0.1 |
| Raisins | 2 Tbsp | 1 Fruit | 0.06 |
| Lemonade, frozen | ¾ cup | 1 Fruit | 0.0 |
| SNACK | | | |
| Corn-Flavored Pop Snack | 150 g | 3 Protein Powder | 0.15 |
| Peach Nectar with Starch Powder | ¼ cup | 1 Fruit | 0.0 |
| | 10 g | 1 Starch Powder | 0.0 |
| LUNCH | | | |
| Pineapple Spinach Chicken | 100 g | 2 Protein Powder | 0.1 |
| Canned Pineapple Chunks Juice Pack (no sugar added) | ¼ cup | 1 Fruit | 0.1 |
| Frozen, chopped Spinach | 1 cup | 2 Vegetable | 0.4 |
| Sesame Cakes | 3 cakes | 1½ Grain | 0.0 |
| Canned Fruit Cocktail Juice Pack (no sugar added) with Starch Powder | 1 cup | 2 Fruit | 0.0 |
| | 10 g | 1 Starch Powder | 0.0 |
| SNACK | | | |
| Mashed Potatoes | 150 g | 3 Protein Powder | 0.15 |
| Diet Beverage | 1 cup | Free | 0.0 |
| with Starch Powder | 10 g | 1 Starch Powder | 0.0 |
| DINNER | | | |
| Hungarian Cabbage Rolls | 100 g | 2 Protein Powder | 0.1 |
| Fresh Onions | ¼ cup | ¼ Vegetable | 0.1 |
| Fresh Mushrooms | ¼ cup | ¼ Vegetable | 0.16 |
| Cabbage Leaves | 2 leaves | 1 Vegetable | 0.13 |
| Tomato Juice and Sauce | ¼ cup | | 0.09 |
| White Long Grain Rice, cooked | ¼ cup | 1 Grain | 0.0 |
| Unsweetened Grapefruit Juice with Starch Powder | ¼ cup | 1 Fruit | 0.1 |
| | 10 g | 1 Starch Powder | 0.0 |
| SNACK | | | |
| Breadsticks | 150 g | 3 Protein Powder | 0.15 |
| Apricot Nectar | ¼ cup | 1 Fruit | 0.1 |
| TOTAL GRAMS OF FAT: | | | 1.99 |
| TOTAL FAT EXCHANGES: | | | 19¾ |
| TOTAL KILOCALORIES: | | | 1806 |
| TOTAL GRAMS OF PROTEIN: | | | 129.1 |

Menu #7 - 1800 Calories

| MEAL | AMOUNT | EXCHANGE | FAT GRAMS |
|---|---|---|---|
| BREAKFAST | | | |
| Crepes - 4 | 200 g | 4 Protein Powder | 0.2 |
| Peach Nectar Sauce with | ¼ cup | 1 Fruit | 0.0 |
| Canned Peaches (no sugar added) and Starch Powder | 4 halves | 2 Fruit | 0.0 |
| | 10 g | 1 Starch Powder | 0.0 |
| Kellogg's Special K | ¾ cup | 1 Grain | 0.0 |
| LUNCH | | | |
| Apple-Vegetable Scramble | 100 g | 2 Protein Powder | 0.1 |
| Fresh Apple, chopped | ½ apple | ½ Fruit | 0.15 |
| Fresh Celery, chopped | 1 stalk | ¼ Vegetable | 0.1 |
| Fresh Onion, chopped | ¼ cup | ¼ Vegetable | 0.1 |
| Fresh Carrot, chopped | ¼ cup | 1 Vegetable | 0.1 |
| Wheat Cakes | 4 cakes | 2 Grain | 0.0 |
| SNACK | | | |
| Banana Loaf | 150 g | 3 Protein Powder | 0.15 |
| Lemonade, frozen concentrate, prepared with Starch Powder | ¾ cup | 1 Fruit | 0.0 |
| | 10 g | 1 Starch Powder | 0.0 |
| DINNER | | | |
| Zucchini Omelet | 50 g | 1 Protein Powder | 0.05 |
| Fresh Zucchini Squash | ½ large | 1 Vegetable | 0.1 |
| "French Fries" | 100 g | 2 Protein Powder | 0.1 |
| Canned Pear Halves Juice Pack (no sugar added) | 4 halves | 2 Fruit | 0.2 |
| SNACK | | | |
| Corn Bread | 150 g | 3 Protein Powder | 0.15 |
| Canned Pineapple Chunks Juice Pack (no sugar added) | ¼ cup | 2 Fruit | 0.2 |
| TOTAL GRAMS OF FAT: | | | 1.70 |
| TOTAL FAT EXCHANGES: | | | 17 |
| TOTAL KILOCALORIES: | | | 1803 |
| TOTAL GRAMS OF PROTEIN: | | | 128.3 |

Representative recipes that were used to prepare the protein products are as follows:

Batter I (Basic Preparation)

Exchange: 8 Protein Powder (composition of Table 2)
Recipe:
Protein Powder   132 grams
Water            270 grams
Instructions:
Mix the dry Protein Powder and water in a mixing bowl until all dry powder is moistened. Transfer the wet mixture to a blender. Blend for 1 minute at high speed. Stop the blender, scrape the sides, and gently stir the

TABLE 3-continued batter. Blend for an additional 1 minute. A fresh batch
of batter should be prepared each day and refrigerated
covered with saran wrap when stored for the day.
Most of the recipes use this batter consistency.

Table to determine amount of batter needed for the day:

| Exchanges: | 8 | 10 | 12 | 14 | 16 |
|---|---|---|---|---|---|
| Protein Powder (grams) | 132 | 165 | 198 | 231 | 264 |
| Water (grams) | 270 | 337 | 404 | 471 | 538 |

Batter II (Basic Preparation)
Exchange: 8 Protein Powder (composition of Table 4)
Recipe:

| | |
|---|---|
| Protein Powder | 132 grams |
| Water | 348 grams |

Instructions:

Mix the dry Protein Powder and water in a mixing bowl
until all dry powder is moistened. Transfer the wet
mixture to a blender. Blend for 1 minute at high speed.
Stop the blender, scrape the sides, and gently stir the
batter. Blend for an additional 1 minute. A fresh batch
of batter should be prepared each day and refrigerated
covered with saran wrap when stored for the day.

Recipes that use this batter consistency include:

Onion Squares
Banana Loaf
Cinnamon raisin bread
Corn bread
Mashed potatoes
Crepes
French toast
Pancakes
Carrot sponge cake
Pumpkin pie squares Table to determine amount of batter needed for the day:

| Exchanges: | 2 | 4 | 6 | 8 | 10 |
|---|---|---|---|---|---|
| Protein Powder (grams) | 33 | 66 | 99 | 132 | 165 |
| Water (grams) | 87 | 174 | 261 | 348 | 435 |

Beef Stir-Fry

| | |
|---|---|
| Exchange: | 2 Protein Powder |
| | 2 Vegetable |

Recipe:

| | |
|---|---|
| Batter I | 100 grams |
| Rich Brown Seasoning | 1 packet |
| Onions, chopped | ¼ cup |
| Frozen Vegetables (thawed) | 1 cup |
| (carrots, zucchini, broccoli, cauliflower) | |

Instructions:

Mix Rich Brown Seasoning with Batter I. Pour into a small
microwave container and cover tightly with lid (snap
seal). Cook on the Defrost cycle for 3¼ minutes. Cut
into small (¼") cubes.
Place onions and thawed vegetables in a non-stick frying
pan. Stir fry over medium heat on the stove until onions
and vegetables are half cooked (not browned). DO NOT
ADD ANY FAT OR SPRAY ON SUBSTANCE LIKE
PAM. Add the beef cubes and continue cooking until the
diced cubes turn golden brown on the edges.
Yield: 1 Serving

Pineapple Spinach Chicken

| | |
|---|---|
| Exchange: | 2 Protein Powder |
| | 2 Vegetable |
| | 1 Fruit |

Recipe:

| | |
|---|---|
| Batter I | 100 grams |
| Golden Seasoning | 2 packets |
| Water | ¼ cup |
| Ginger, Ground | ¼ tsp |
| Equal | as desired (suggest 7 packets) |
| Frozen Chopped Spinach (thawed) | 1 cup |
| Pineapple chunks, Juice packed, (drained) | ¼ cup |

Instructions:

Add one packet of golden seasoning to the Batter I and mix
well. Pour into a small microwave container and cover
tightly with a lid (snap seal). Cook on the Defrost cycle
for 3¼ minutes. Cut into bite size pieces.
Place other packet of golden seasoning, water, Equal, and
ginger in a sauce pan. Cook over medium heat, stirring
occasionally until mixture comes to a boil. Add
chicken-flavored pieces, spinach, and pineapple to the
boiling mixture. Cover, reduce heat, and simmer for
10 minutes.
Yield: 1 Serving

French Fries
Exchange: 2 Protein Powder
Recipe:

| | |
|---|---|
| Batter I | 100 grams |
| Potato Flavor | pinch (3 grams) |

Instructions:

Thoroughly mix Batter I and the potato flavor using a wire
whisk or fork. Spread the mixture evenly into a small
microwave container and cover tightly with a lid (snap
seal) or plastic wrap. Cook on the Defrost cycle for
2 minutes 30 seconds. Cool and place removed loaf on a
dish. Cut the loaf width wise into ¼ to ½ inch
strips. Stir fry the strips in a non-stick frying pan
until golden brown on all sides. DO NOT ADD FAT OR
SPRAY ON SUBSTANCE LIKE PAM.
Yield: 1 Serving

Mashed Potatoes
Exchange: 2 Protein Powder
Recipe:

| | |
|---|---|
| Batter II | 100 grams |
| Potato Flavor | 3 grams |

Instructions:

Thoroughly mix Batter II and the potato flavor using a
wire whisk or fork. Pour batter into a non-stick frying
pan. DO NOT ADD FAT OR SPRAY ON SUBSTANCE
LIKE PAM. Cook over medium heat with constant stirring
until desired texture (scrambled egg like) is achieved.

*non-diabetic
**diabetic

Thus, the arginine enriched whey protein isolate may be formulated into substantially fat free, controlled calorie enteral foods which deliver protein having a hypocholesterolemic amino acid profile when digested and absorbed.

It would appear that plasma cholesterol levels in humans can be significantly reduced and controlled, and coronary atherosclerosis arrested and reversed by maintaining such persons for an extended period, such as, for example, 3 weeks to 3 months, on a substantially fat free, controlled calorie diet, such as the seven day rotational diet disclosed above, utilizing the arginine enriched, whey protein isolate composition of this invention.

What is claimed is:

1. A composition for use in preparing substantially fat free enteral foods for use in the treatment of atherosclerosis which comprises whey protein and an amount of L-arginine sufficient to provide the composition with a hypocholesterolemic amino acid profile.

2. The composition defined in claim 1 in which said whey protein is whey protein isolate containing at least 95% protein (dry basis) and less than 1% fat and lactose.

3. The composition defined in claim 2 in which the arginine is present in an amount of about 0.16 parts by weight per part by weight of the whey protein isolate.

4. An enteral diet for use in the treatment of hypercholesterolemia which comprises substantially fat free foods formulated from a mixture of whey protein and an amount of L-arginine to provide the mixture with a hypocholesterolemic amino acid profile.

5. The enteral diet defined in claim 4 in which the diet provides less than 2 grams fat per day, with less than 1% of the calories being derived from fat.

6. The enteral diet defined in claim 4 in which the whey protein is whey protein isolate containing at least 95% protein (dry basis) and less than 1% fat and lactose.

7. A method of reducing plasma cholesterol in patients having elevated cholesterol levels which comprises maintaining the patients on a substantially fat free, high protein enteral diet in which the protein has a hypocholesterolemic acid profile provided by a mixture of whey protein and L-arginine for a period of time sufficient to reduce plasma cholesterol levels.

8. The method defined in claim 7 in which the diet provides less than 2 grams of fat per day, with less than 1% of the calories being derived from fat.

9. The method defined in claim 8 in which the whey protein is whey protein isolate containing over 95% protein (dry basis) and less than 1% fat and lactose, with the protein being substantially undenatured.

* * * * *